(12) United States Patent
Doyen et al.

(10) Patent No.: US 11,597,902 B2
(45) Date of Patent: *Mar. 7, 2023

(54) BIOMASS MEMBRANE CONTACTOR

(71) Applicant: VITO NV (VLAAMSE INSTELLING VOOR TECHNOLOGISCH ONDERZOEK NV), Mol (BE)

(72) Inventors: Willy Doyen, Mol (BE); Bart Molenberghs, Mol (BE); Helene De Wever, Mol (BE); Mahboubi Soufiani Amir, Boras (SE); Mohammad Taherzadeh, Hisings Backa (SE)

(73) Assignee: VITO NV (VLAAMSE INSTELLING VOOR TECHNOLOGISCH ONDERZOEK NV), Mol (BE)

( * ) Notice: Subject to any disclaimer, the term of this patent is extended or adjusted under 35 U.S.C. 154(b) by 1102 days.

This patent is subject to a terminal disclaimer.

(21) Appl. No.: 16/308,372

(22) PCT Filed: Jun. 2, 2017

(86) PCT No.: PCT/EP2017/063579
§ 371 (c)(1),
(2) Date: Dec. 7, 2018

(87) PCT Pub. No.: WO2017/211750
PCT Pub. Date: Dec. 14, 2017

(65) Prior Publication Data
US 2019/0211298 A1    Jul. 11, 2019

(30) Foreign Application Priority Data
Jun. 8, 2016 (EP) .................................. 16173481

(51) Int. Cl.
*C12M 3/00* (2006.01)
*B01D 61/00* (2006.01)
(Continued)

(52) U.S. Cl.
CPC ............. *C12M 29/04* (2013.01); *B01D 61/18* (2013.01); *B01D 63/082* (2013.01); *B01D 65/08* (2013.01);
(Continued)

(58) Field of Classification Search
CPC ...... C12M 29/04; C12M 27/22; B01D 63/082
See application file for complete search history.

(56) References Cited

U.S. PATENT DOCUMENTS

| 2003/0077816 A1* | 4/2003 | Kronenthal | ............ C12M 21/08 |
| | | | 435/297.2 |
| 2004/0178147 A1* | 9/2004 | Fanselow | ............... B01D 63/10 |
| | | | 210/644 |

(Continued)

FOREIGN PATENT DOCUMENTS

| EP | 0662341 A1 | 7/1995 |
| WO | 90/13639 A1 | 11/1990 |
| WO | 2016/060892 A1 | 4/2016 |

OTHER PUBLICATIONS

International Search Report and Written Opinion from International Application No. PCT/EP2017/063579, dated Aug. 30, 2017.

*Primary Examiner* — Nathan A Bowers
(74) *Attorney, Agent, or Firm* — Merchant & Gould P.C.

(57) ABSTRACT

An assembly includes a housing with opposite first and second layers. The first and second layers are spaced apart to define a confined interior space. A semi-permeable membrane is attached to the first layer, the semi-permeable membrane covering a porous area portion of the first layer. An outlet port and an inlet port are in fluid communication with the interior space. The assembly includes a first circulator for circulating a first fluid between the outlet port and the inlet port, and a second circulator for circulating a second fluid along an exterior surface of the semi-permeable membrane. The second circulator includes a fluid duct
(Continued)

attached to or integrated within the housing. The fluid duct is isolated from the interior space and is porous to provide fluid access to an exterior surface of the semi-permeable membrane. The semi-permeable membrane forms a barrier allowing exchange of compounds across the membrane.

11 Claims, 9 Drawing Sheets

(51) Int. Cl.

| | | |
|---|---|---|
| *C12M 1/00* | (2006.01) | |
| *B01D 61/18* | (2006.01) | |
| *B01D 63/08* | (2006.01) | |
| *B01D 65/08* | (2006.01) | |
| *C12M 1/12* | (2006.01) | |
| *C12P 1/02* | (2006.01) | |
| *C12P 1/04* | (2006.01) | |

(52) U.S. Cl.
CPC ............ *C12M 23/04* (2013.01); *C12M 23/42* (2013.01); *C12M 27/22* (2013.01); *C12M 29/10* (2013.01); *C12M 29/24* (2013.01); *C12P 1/02* (2013.01); *C12P 1/04* (2013.01); *B01D 2311/04* (2013.01); *B01D 2311/2688* (2013.01); *B01D 2313/086* (2013.01); *B01D 2313/21* (2013.01); *B01D 2313/26* (2013.01); *B01D 2315/06* (2013.01); *B01D 2321/185* (2013.01)

(56) References Cited

U.S. PATENT DOCUMENTS

| | | | |
|---|---|---|---|
| 2007/0125697 A1* | 6/2007 | Lee | C02F 1/44 |
| | | | 210/321.69 |
| 2015/0027948 A1* | 1/2015 | Doyen | B01D 63/081 |
| | | | 210/636 |
| 2018/0328823 A1* | 11/2018 | Olivier | B01D 63/087 |
| 2019/0105609 A1* | 4/2019 | Zhang | B01D 61/147 |
| 2019/0127251 A1* | 5/2019 | Rogalla | C02F 3/006 |

* cited by examiner

FIG 4: A-A

BIOMASS MEMBRANE CONTACTOR

This application is a National Stage Application of International Application No. PCT/EP2017/063579, filed 2 Jun. 2017, which claims benefit of Ser. No. 16/173,481.9, filed 8 Jun. 2016 in Europe and which applications are incorporated herein by reference. To the extent appropriate, a claim of priority is made to each of the above disclosed applications.

FIELD OF THE INVENTION

The present invention is related to membrane assemblies defining an enclosed space for encapsulating cells for use in biotechnological applications, such as but not limited to product generation and recovery from fermentation broths containing considerable amounts of inhibitory compounds.

BACKGROUND

Membrane bioreactors (MBRs) are considered for use in biotechnological applications for producing and recovering compounds of interest from complex biomass feeds. There are different benefits sought by utilization of membrane bioreactors in these applications, amongst others the ease of product recovery as a result of high separation efficiency of the membranes, high product yield and biological conversion rate due to high cell concentration, low energy demand and ease of operation in continuous mode. However, conventional MBRs show limitations for bioconversions of certain feed streams. In particular, handling feed sources containing a high concentration of inhibitory compounds or containing several different substrates is inefficient. Moreover, feeds with high suspended solid (SS) content are problematic in that they negatively affect cell/medium separation.

In order to cope with the above drawbacks, membranes are being used to encapsulate cells and/or enzymes inside so called membrane pockets or sachets. Through cell encapsulation, a high local cell concentration is provided inside the membrane pocket which is kept separated from the main bioreactor medium by a synthetic semi-permeable membrane. This microenvironment gives the cells the ability to tolerate high inhibitor content and also co-utilize different substrates in the feed which reach the cell through diffusion through the membrane. Experiments have indicated that cell encapsulation through membranes allows for increasing bioconversion efficiency. The above encapsulated cell applications are referred to as reverse MBR since the bioreactions occur at the inside of the membrane pockets while the feed is at the outside.

It is known from WO 2016/060892, University of South Florida, 21 Apr. 2016, an algae cultivation system including a passive membrane photobioreactor container having an interior space in which algae can be cultivated and a porous membrane that separates growth media from the interior space. Water, carbon dioxide, and nutrients contained within the growth media can pass through the membrane and into the interior space but microbial contaminants cannot. A recirculation system is provided in fluid communication with the interior space via a container outlet and a container inlet. The recirculation system includes a pump mechanism that is used to draw algae from the interior space and a dewatering mechanism that is used to dewater the algae so that concentrated algae sludge can be output from the system and collected. The recirculation system then pumps the remaining algae and water back into the interior space for further algae cultivation. The photobioreactor container can include multiple laterally extending baffles provided within the interior space that force the algal culture to travel a serpentine path through the container from the inlet to the outlet. This improves mixing, prevents internal biofouling, and potentially increases the concentration gradient between the growth media and algal culture as it prevents short circuiting in which the algae does not have enough time to grow.

SUMMARY

Since the exchange of compounds through the membrane is principally diffusion-based, it would be desirable to be able to better control diffusion processes through the membrane. It would also be desirable to facilitate or improve the exchange or diffusion of compounds, such as substrates, nutrients and metabolite products, through the membrane.

According to aspects of the present disclosure, there is therefore provided an assembly. The assembly can generally comprise, or be referred to as, a membrane cartridge and is advantageously suitable for use in reverse membrane bioreactor and/or other membrane contactor applications.

The assembly comprises a housing and at least one semi-permeable membrane. The housing comprises a first layer and a second layer opposite the first layer, wherein the first layer and the second layer are spaced apart to define a confined interior space. The semipermeable membrane is attached to the first layer and covers an area portion of the first layer, referred to as a membrane area portion. The first layer is porous across the membrane area portion. The semi-permeable membrane forms a barrier allowing for exchange of compounds across the semi-permeable membrane, such as between a fluid comprised in the interior space and a fluid at the exterior side of the membrane.

According to a first aspect, the assembly comprises a first outlet port and a first inlet port in fluid communication with the interior space. The assembly comprises first means for (re)circulating a first fluid between the first outlet port and the first inlet port. The first means is advantageously a gas recirculation system, which may comprise a gas pump mechanism. Alternatively, it can comprise a liquid pump, or a combination of both a gas pump and a liquid pump.

According to a second aspect, which can be optional, or can be provided in combination or alternative to the first aspect, the assembly comprises second means for circulating a second fluid along a surface of the semi-permeable membrane opposite the interior space, e.g. at the exterior surface. The second means is advantageously at least partially integrated in the housing of the assembly, possibly below the semi-permeable membrane. The second means is advantageously a gas bubbling system, advantageously providing coarse bubbling to an exterior surface of the semipermeable membrane. The housing advantageously comprises a fluid supply port in fluid communication with the second means. The second means advantageously comprises a fluid duct or compartment comprising through-holes for gas bubbling, which fluid compartment is advantageously in vertical alignment with the interior space and is advantageously attached to or integrated in the housing. The fluid duct is advantageously isolated from the interior space through an (gas) impermeable separating wall or barrier arranged between the interior space and the fluid duct. The fluid duct is porous towards an external side of the housing to provide fluid access to an exterior surface of the semi-permeable membrane.

The combined provision of the first and second aspects in an assembly of the above kind allows for simultaneously refreshing liquids/fluids at both sides of the semi-permeable membrane, which greatly improves diffusion through the semi-permeable membrane and allows better operational control and more uniform operation of such assemblies in reverse membrane bioreactor and/or membrane contactor applications coupled to biotechnological processes. This is true for the diffusion of compounds from the exterior side of the membrane to the interior space of the assembly and is advantageously also true for any diffusion of products from the interior space of the assembly to the exterior side, where the products can be collected/harvested according to possibly known techniques. Furthermore, an independent control of operational conditions for the (exterior) feed and the (interior) encapsulated biomass becomes possible herewith.

Yet a further advantage of an integration of the first and the second aspects in a single assembly is that it reduces the overall complexity and footprint of bioreactors.

According to further aspects of the present disclosure, there is provided an apparatus for recovering first compounds through conversion of second compounds. The apparatus comprises at least one assembly as disclosed herein arranged in a vessel. The apparatus further comprises a supply for the second compounds. The second compounds can e.g. be provided in a liquid feed. The supply for the second compounds can be arranged for supplying the second compounds in the vessel, at the exterior of the assembly, or directly in the interior space of the assembly, e.g. through a suitable supply port. A first biomass, advantageously at least in part liquid, and advantageously comprising microorganisms, such as cells, and/or enzymes capable of converting the second compound into a first compound, is arranged in the interior space of the at least one assembly. The at least one assembly is arranged in the vessel, and is advantageously at least partially immersed in a liquid contained in the vessel. The apparatus further comprises a fluid supply connected to the fluid supply port of the at least one assembly. The first means for circulating a first fluid and the second means for circulating a second fluid of the at least one assembly allow for the second compound and/or the first compound to be brought in contact with a surface of the semi-permeable membrane. The semi-permeable membrane has characteristics such that it allows the first compounds and/or the second compounds to be transported across the membrane through suitable transport mechanisms, such as, though not limited to, diffusion. It will be convenient to note that the liquid contained in the vessel can comprise a second biomass, which is arranged at the exterior of the at least one assembly. The semi-permeable membrane is advantageously impenetrable to the first biomass, the second biomass, or both. The second biomass is e.g. capable of converting the first compounds, e.g. following transport of the first compounds from the interior space across the semi-permeable membrane, into a third compound.

According to yet further aspects of the present disclosure, there is provided a use of the assemblies as disclosed herein, and/or the apparatus as disclosed herein for recovering compounds from a fermentation broth.

Methods of manufacturing and of operating assemblies of the above kind are described herein as well.

DESCRIPTION OF THE DRAWINGS

Aspects of the invention will now be described in more detail with reference to the appended drawings, which are illustrative, and wherein same reference numerals illustrate same or similar features, wherein:

FIG. 5 represents a reverse membrane bioreactor in which a plurality of assemblies of FIG. 1 and/or FIG. 3 are disposed and comprising an air supply system for bubbling the feed within the bioreactor;

DETAILED DESCRIPTION

Figure 1:
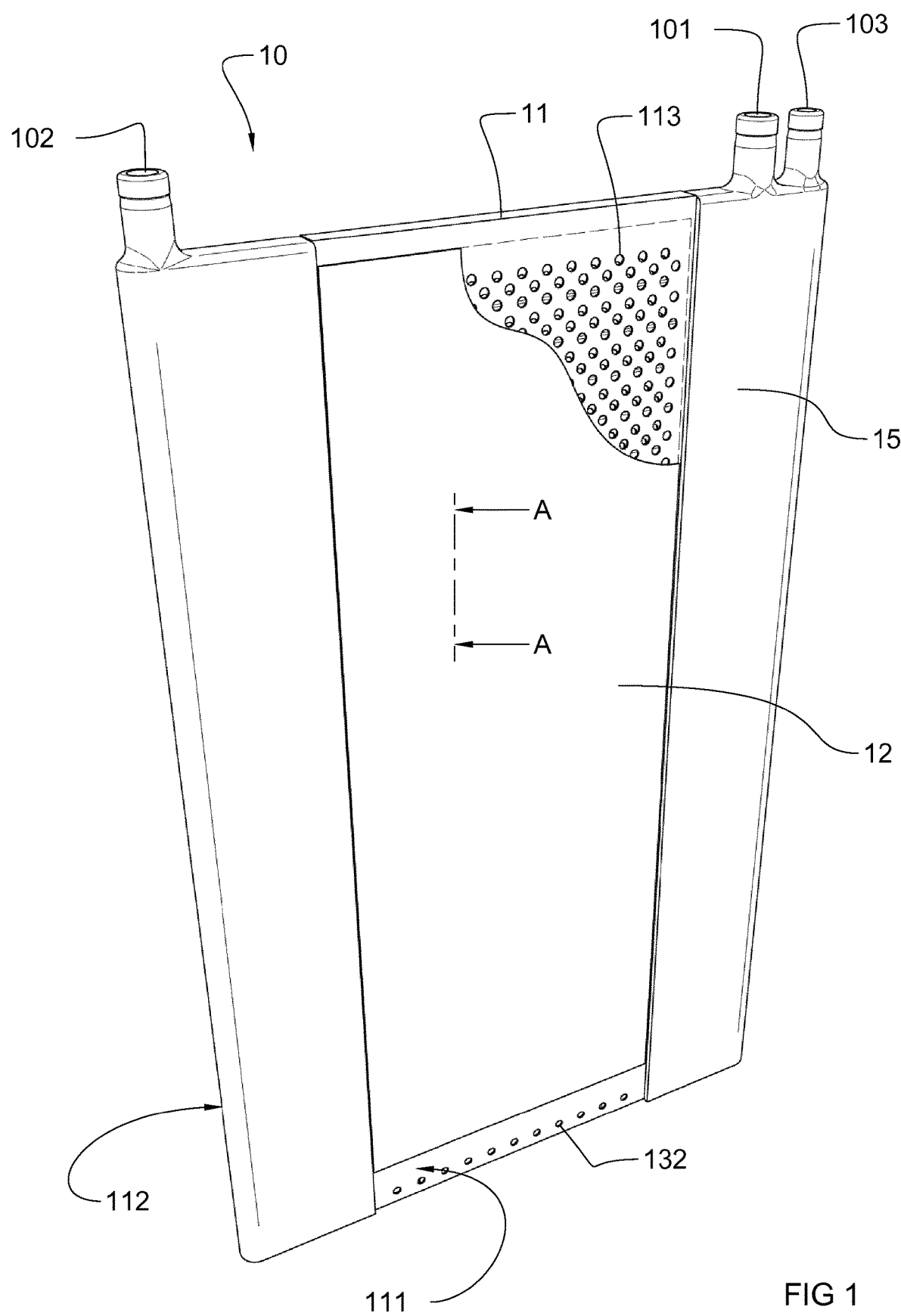
FIG. 1 represents a perspective view of a housing and attached membrane of assemblies according to aspects disclosed herein.
Figure 2:
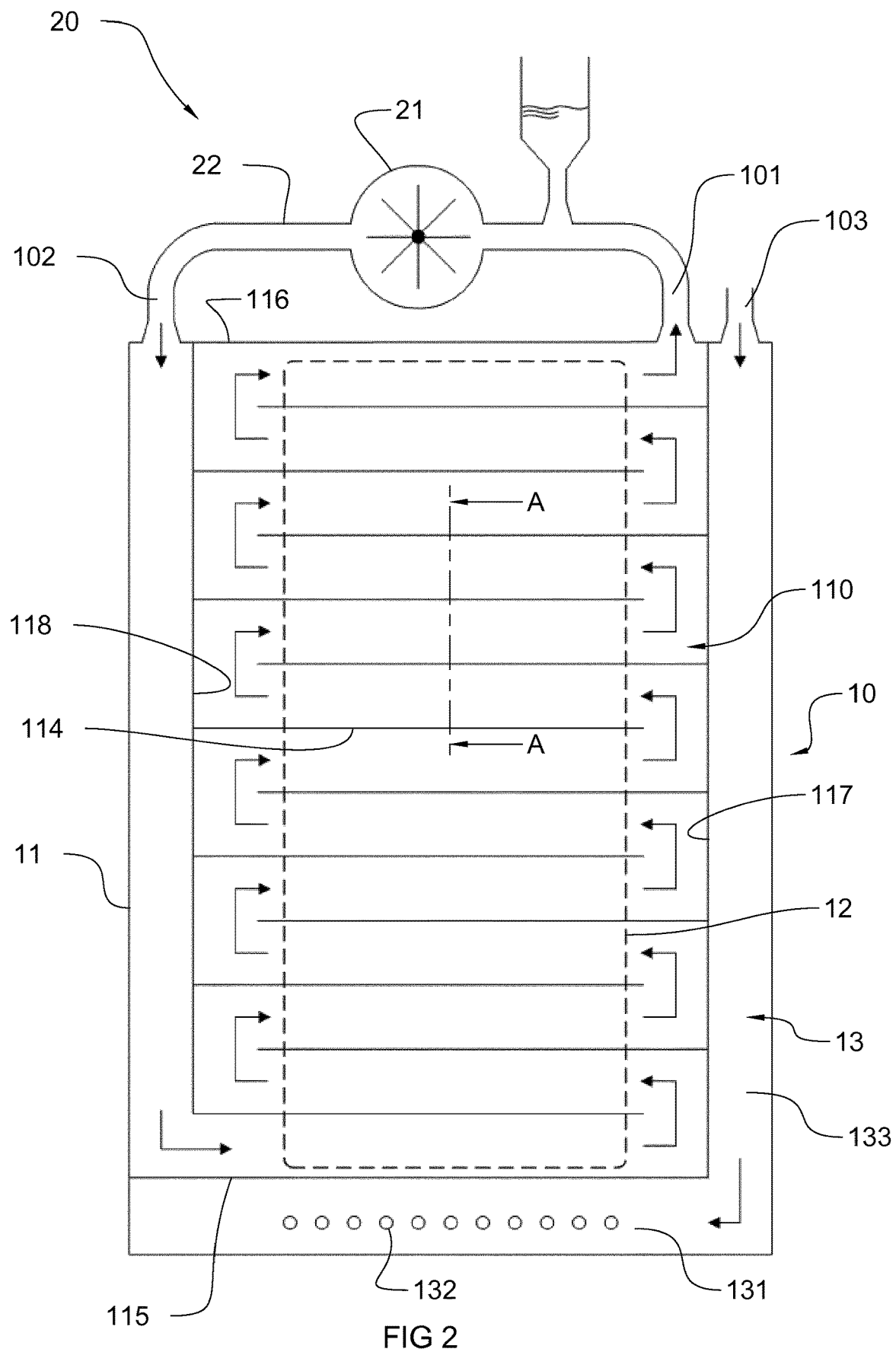
FIG. 2 represents a vertical cross-sectional view of an assembly comprising the housing and membrane of FIG. 1.

Referring to FIGS. 1 and 2, advantageous examples of an assembly 10, hereinafter referred to as membrane assembly, comprise a container like housing 11 with an interior space 110 interposed between a front exterior layer 111 and a back exterior layer 112 of the housing 11. The front exterior layer 111 and the back exterior layer 112 are advantageously planar and form an exterior shell of housing 11 which is closed along the edges of layers 111 and 112.

A semi-permeable membrane 12 is attached to front layer 111, advantageously on an exterior surface of layer 111. Another semi-permeable membrane may be attached to back layer 112 (not shown) to advantageously form a symmetrical cartridge relative to a vertical (median) plane of the housing 11 parallel to layers 111 and 112. The semi-permeable membrane 12 covers an area portion of front layer 111 referred to as the membrane area portion. Other area portions of the front layer 111, such as at the edges, may not be covered by the semi-permeable membrane 12.

The exterior shell of housing 11, and in particular the front layer 111 and the back layer 112 are advantageously made of an impermeable, or a nonporous material. Suitable materials are thermoplastic materials, such as polyvinyl chloride (PVC), polymethyl methacrylate (PMMA), polycarbonate (PC), Acrylonitrile Butadiene Styrene (ABS), polyethylene (PE), polystyrene (PS), polypropylene (PP), etc. The impermeability of the material of layer 111 may be evaluated for water at 0.1 bar differential pressure, possibly at 1 bar liquid differential pressure, possibly at 5 bar differential pressure. The non-porosity of the material of layer 111 refers to the absence of interconnected pores which would provide for a fluid path from one surface to the opposite surface of layer 111. In an area portion of the front layer 111, and possibly of the back layer 112 as well, referred to as the membrane area portion, the respective front layer 111 or back layer 112 is porous, e.g. by having the impermeable material of layer 111 perforated with through openings 113.

Through openings 113 provide for a fluid path between the interior space 110 and the semi-permeable membrane 12, such that compounds may diffuse through membrane 12 and be exchanged between the interior space 110 and the exterior of cartridge 10. In this respect, the semi-permeable membrane 12 acts as a barrier controlling which compounds will diffuse and which ones will be retained at either side of membrane 12.

A semi-permeable membrane—in short membrane—as referred to in the present description refers to a layer or sheet of a solid, continuous and advantageously porous material having a structure/composition allowing one or more compounds to be selectively transported through the membrane and hence enabling to separate the one or more compounds from a feed, which can be liquid or gaseous. A membrane hence features a determined permeability for the one or more compounds. The permselectivity can be determined by any kind of separation mechanism, such as but not limited to one or a combination of: a characteristic pore size of the membrane (e.g. microporous or nanoporous membranes), a characteristic attraction of specific charge types (e.g. an ion exchange membrane), selective sorption, and solution diffusion characteristics. The membranes advantageously have characteristic pore size between 0.001 μm and 10 μm.

The membranes as referred to in the present description are advantageously configured for exchange or diffusion of compounds by one or more of: membrane bioreactors, reverse membrane bioreactors, enzyme reactors, membrane contactors, in-situ product recovery, coculture bioconversion processes. The membranes can be quite open membranes like microfiltration, ultrafiltration, membrane distillation, but can also be dense membranes like nanofiltration, reverse osmosis, pervaporation, or ion-exchange membranes.

Figure 5:
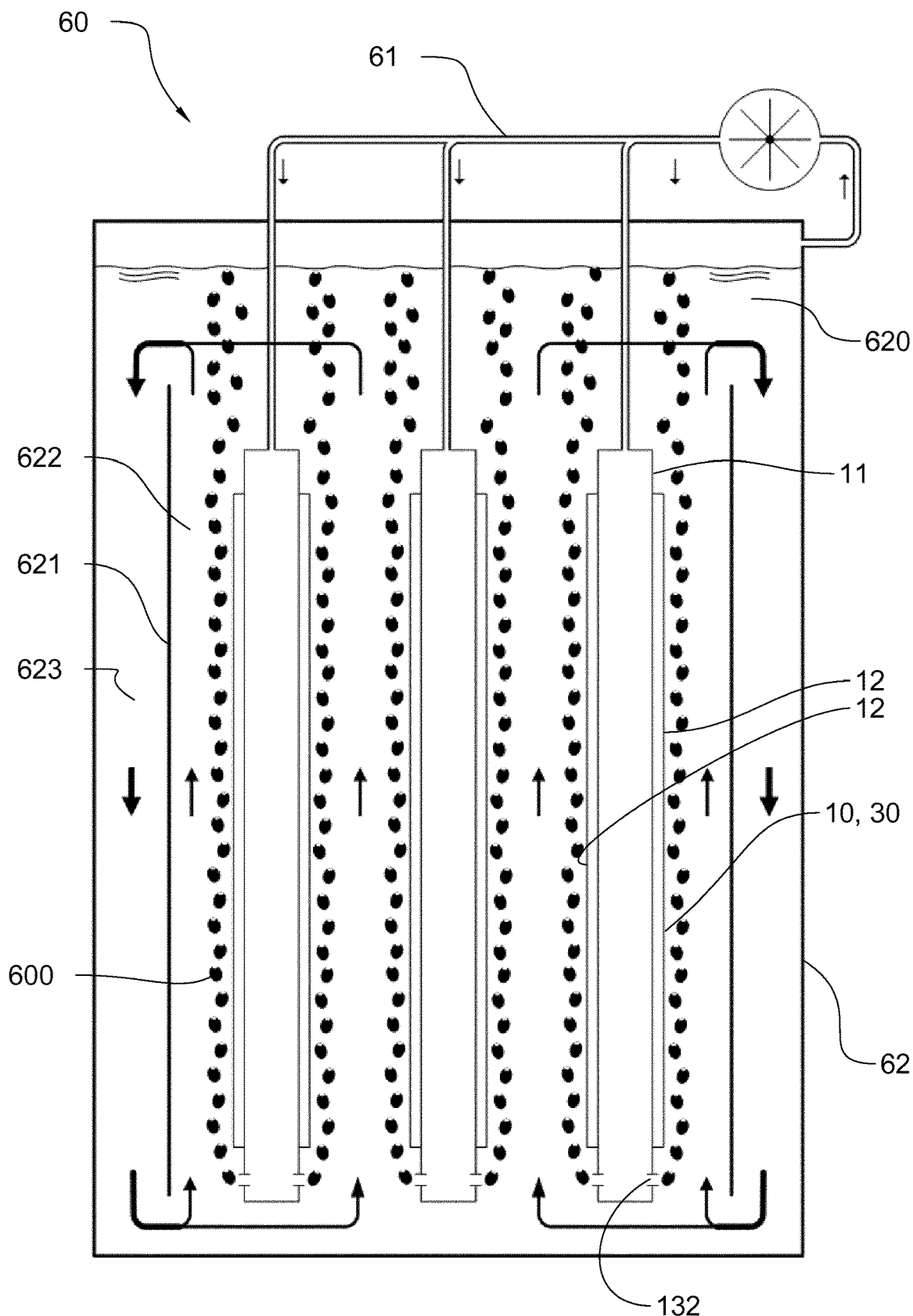

The assembly 10 is advantageously intended for use in reverse membrane bioreactor applications. Referring to FIG. 5, biomass comprising microorganisms and/or enzymes are arranged into the interior space of cartridge 10, where these microorganisms and/or enzymes remain encapsulated. The cartridge 10 is immersed in a bioreactor vessel 62 comprising a substrate or feed 620 which is made to contact the membrane 12. Membrane 12 allows feed compounds for the microorganisms and/or enzymes to migrate from the surrounding substrate 620 to the interior space 110, where the feed compounds will be used by the microorganisms and/or enzymes to produce desired products. The desired products may be allowed to migrate through membrane 12 into the feed 620 surrounding cartridge 10, or be harvested directly from the cartridge.

It will be convenient to note that other configurations are contemplated in the present description. By way of example, the biomass can be arranged at the exterior of the assembly 10, and feed compounds, such as nutrients, can be dosed from the interior space to the exterior through the membrane. Alternatively, different kinds of biomass, referred to as cocultures, can be arranged at opposite sides of the membrane (one in the interior space, the other one at the exterior).

Biomass as referred to in the present description can comprise or consist of bacteria, yeasts, fungi, wild type or (genetically) modified strains, single cultures, cocultures or mixed cultures. The biomass can comprise or consist of enzymes, such as immobilized enzymes, free enzymes, CLEAs—crosslinked enzyme aggregates, modified enzymes, single enzymes or enzymes combinations.

As indicated above, such technique of cell encapsulation is particularly advantageous in biotechnological applications with complex feeds that contain relatively high concentrations of inhibitory compounds. In such applications, the migration of compounds through the semi-permeable membrane 12 is principally diffusion controlled. Advantageously, no practical pressure difference across membrane 12 is maintained, which differentiates reverse membrane bioreactor applications with classical membrane bioreactor applications.

It will be convenient to note that even though in theory it is desirable to have no pressure difference across the membrane, a slight pressure difference may not be avoided for technical reasons, such as due to the structure or configuration of assembly 10. In operation, such a pressure difference across the membrane 12 advantageously will not exceed 1 bar, advantageously will not exceed 0.5 bar, advantageously will not exceed 0.3 bar, advantageously will not exceed 0.15 bar, advantageously will not exceed 0.08 bar.

The diffusion of compounds through the membrane 12 can be improved by refreshing the compounds present at either one or both sides of membrane 12. To this end, and referring to FIG. 2, a system 20 for recirculating the fluid (liquid including the biomass) inside the interior space 110 is provided. The housing 11 comprises an outlet port 101 and an inlet port 102 in fluid communication with the interior space 110 and connected to recirculation system 20. Recirculation system 20 can comprise a pump mechanism 21 in fluid communication with the outlet port 101 and the inlet port 102 of housing 11 through a suitable duct system 22. The pump mechanism 21 operates to maintain a fluid flow from the outlet port 101 to the inlet port 102.

Each assembly 10 may comprise its proper recirculation system 20, which can be integrated within housing 11. Alternatively, recirculation system 20 can be in common between multiple housings. In the latter case, the duct system 22 would comprise collection and distribution manifolds (not shown) connecting respectively the outlet ports 101 and the inlet ports 102 of multiple housings 11 and a single pump mechanism 21 between the manifolds.

Pump mechanism 21 can be a liquid pump in order to pump the liquid contained within interior space 110 from the outlet port 101 to the inlet port 102. In such case, the microorganisms and/or enzymes may flow through pump mechanism 21.

The housing 11 advantageously comprises baffles 114 extending transversely within the interior space 110 that force the liquid (biomass) present within the interior space to travel a serpentine path through the interior space, from the inlet port 102 to the outlet port 101. Baffles 114 advantageously extend between the front layer 111 and the back layer 112. Baffles 114 may extend transverse through the interior space 110 in any suitable direction, such as horizontal as shown in FIG. 2, oblique or vertical.

Figure 3:
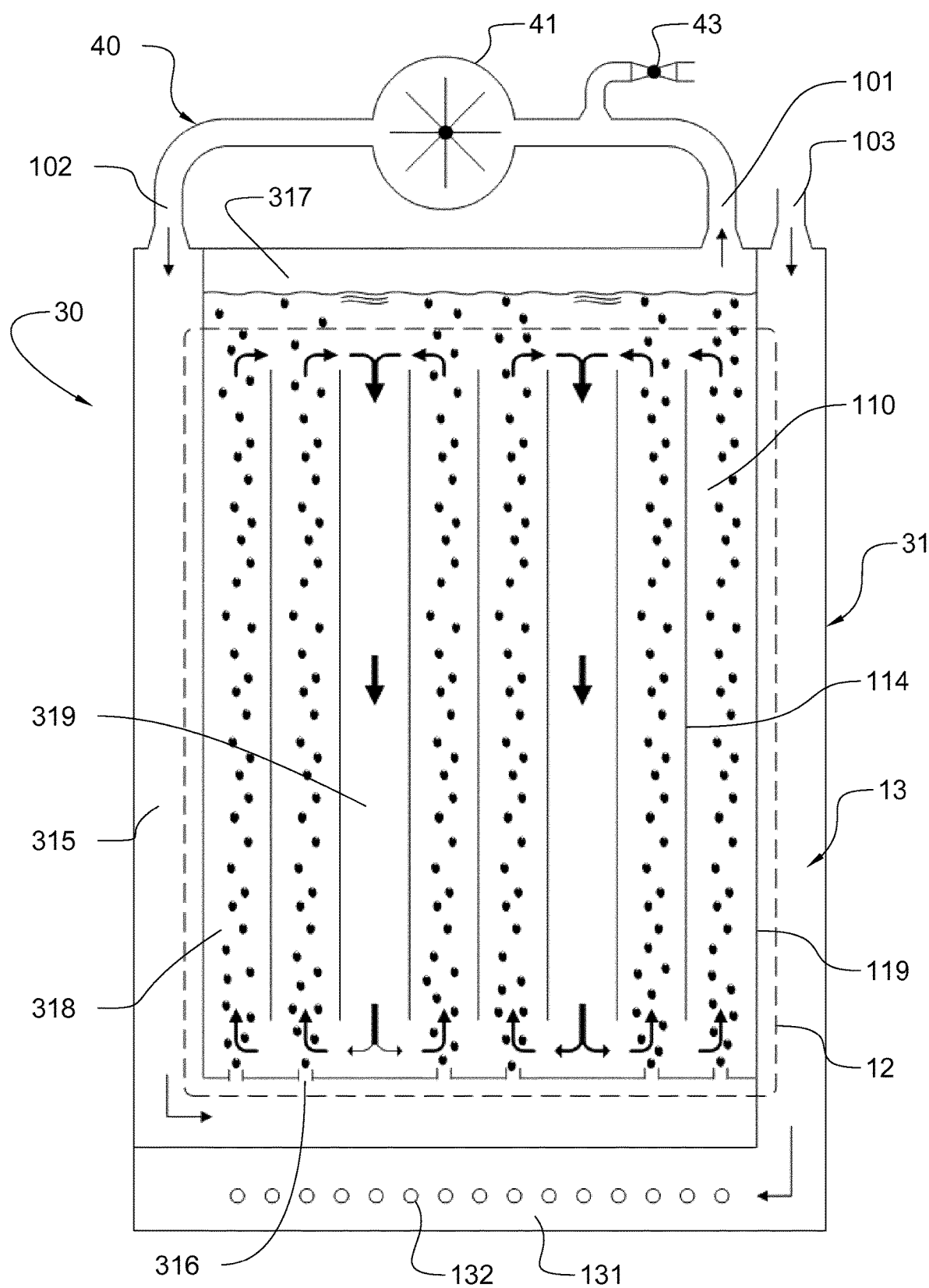
FIG. 3 represents a vertical cross-sectional view of another assembly according to aspects disclosed herein.

Alternatively, referring to FIG. 3, an assembly 30 is shown comprising a recirculation system 40. Recirculation system 40 differs from recirculation system 20 of FIG. 2 in that pump mechanism 41 is configured as a gas pump mechanism in order to pump a gas through inlet port 102 into the interior space 110. This gas is collected at the outlet port 101 and recirculated. As a further difference with respect to assembly 10, assembly 30 may comprise a gas duct 315 in fluid communication with inlet port 102 and which communicates with interior space 110 through nozzles 316 configured for injecting the gas pumped through recirculation system 40 in the form of gas bubbles into the interior space 110. The gas bubbles provide for coarse bubbling of the liquid (biomass) present within interior space 110. In such case, baffles 114 are advantageously oriented to allow an upwards flow of the gas bubbles, which are subsequently collected in a gas collector 317 provided at a top end of the housing 31 and in fluid communication with the outlet port 101. The baffles may be oriented vertically or obliquely. The liquid (biomass) which is entrained to flow upwards along with the gas bubbles in upward flow compartments 318 is recirculated in interior space 110 by providing one or multiple downward flow compartments 319, which may be separated from compartments 318 by baffles 114. As a result, recirculating the gas through recirculation system 40 allows also for recirculating the liquid (biomass) contained in interior space 110, which additionally may be forced to travel a serpentine path in interior space 110.

The recirculated gas is advantageously a co-product of the microorganisms and/or enzymes in the biomass of interior space 110. In case of aerobic processes/fermentation, the gas can be air, oxygen, hydrogen, carbon dioxide, or a combination thereof. In case of anaerobic processes/fermentation, the gas can be methane, carbon dioxide, hydrogen, nitrogen or a combination thereof. A vent 43 may be provided in recirculation system 40 for venting/collection of any surplus of gas. It will be convenient to note that any gas that may be produced by the biomass inside interior space 110 will generally not be able to penetrate through the membrane 12, since the pressure at the interior space is typically lower than the bubble point pressure of the membrane 12.

One advantage of recirculation system 40 over recirculation system 20 is that the useful microorganisms and/or enzymes encapsulated within the interior space 110 experience a much lower shear compared to recirculation system 20 since they do not need to pass through the pump mechanism, while maintaining a high liquid refreshment rate at the interior surface of the membrane 12. Another advantage is that the gas bubbling may provide for a scouring effect at the interior surface of the membrane, keeping the surface clean. Yet an additional advantage is that the operational cost of a gas recirculation system 40 is typically lower compared to a liquid recirculation system 20.

The recirculation systems 20 and 40 both allow to recirculate the liquid (biomass) contained within interior space 110 and thereby refreshing the liquid in contact with the interior side of membrane 12. This prevents formation of a biofilm at the interior side and improves the exchange of compounds through the membrane 12 by diffusion.

Figure 4:
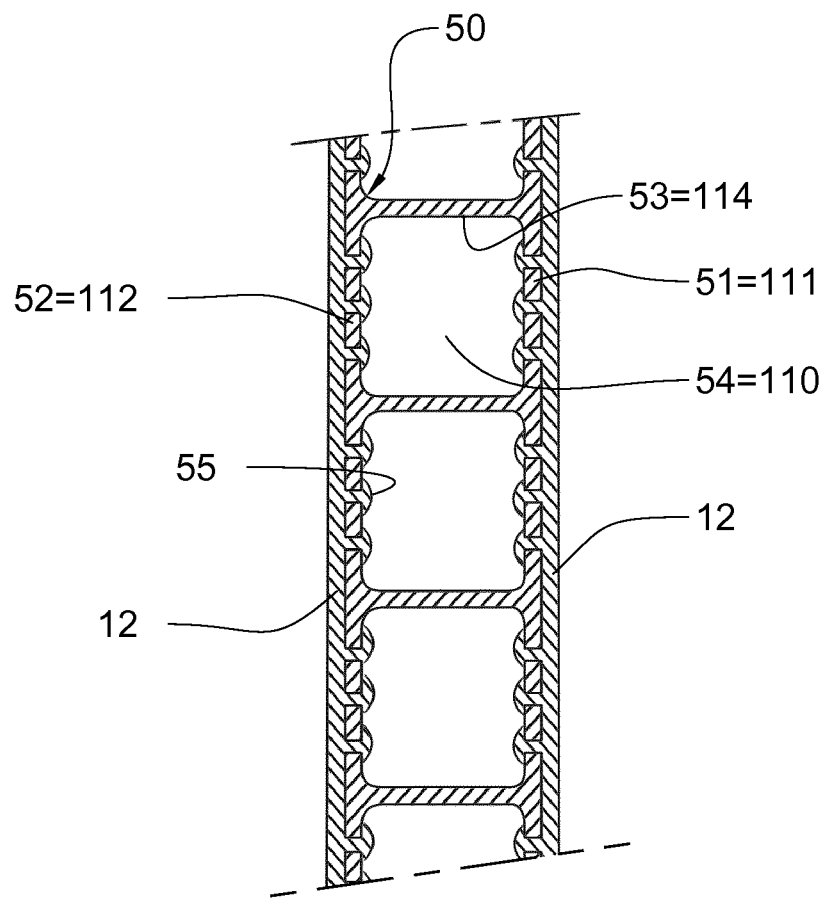
FIG. 4 represents a cross-section according to section line A-A of the assemblies of FIG. 1, showing a possible internal structure of the housing.

In order to avoid any stagnant zones in the interior space 110, the layers 111 and possibly 112 are advantageously made of a dense or nonporous thermoplastic polymer sheet, which allows having a smooth wall of the interior space 110. An advantageous way of providing the housing 11 and 31 is by using so-called multi-walled boards or panels. Suitable structures for the housing are e.g. double or multi-walled polycarbonate sheets, such as Makrolon® multi UV sheets (Bayer, Germany). A cross-section of the housing 11 or 31 showing a double walled sheet of the above kind is represented in FIG. 4. Double walled sheet 50 comprises opposite exterior layers 51 and 52 which are spaced apart and connected through continuous web members 53. Web members 53 are spaced apart to define channels 54 between the exterior layers 51 and 52 and between consecutive web members 53. It is easy to see that panel 50 is advantageously used in assemblies 10 and 30, with the exterior layers 51 and 52 forming the front and back layers 111 and 112, which can be perforated to provide through-holes 113, and web members 53 forming baffles 114. Other suitable examples are POLISNAKE® polycarbonate panels (Politec Polimeri Tecnici SA, Switzerland) described in EP 1543945, and polypropylene KIBO X-panels and KIBO M-panels (KIBO Kunststoffe GmbH, Germany). Laminated panels, such as tri-laminates made by lamination of two sheets to double side ribbed sheet, or such as bi-laminates (two laminated ribbed sheets), can be suitable as well. Suitable manifold-like edge caps 14, 15, as shown in FIG. 1, can be attached to the edges of panels 50 to obtain the assemblies 10 and 30. The fluid ports 101, 102, 103 can easily be integrated in the edge caps 14, 15. Alternatively, layers 111 and 112 can be formed of advantageously thermoplastic polymer sheets which comprise embossments that define the interior space 110 and any additional fluid compartment as described below. The layers 111 and 112 are bonded along the edges of the embossments to seal the compartments. Such housings are described in PCT application No. PCT/EP2017/063544 filed on 2 Jun. 2017. The distance between the front layer 111 and the back layer 112, i.e., the thickness of the interior space 110, is advantageously between 3 mm and 20 mm, advantageously at least 5 mm.

Referring again to FIG. 1-3, the membrane assemblies 10 and 30 advantageously comprise means for entraining a flow of the liquid substrate or feed at the exterior side of the membrane 12 which is advantageously integrated into the assembly. To this end, the housing 11, 31 comprises a duct system 13 which is isolated or separate from the interior space 110. Duct system 13 comprises a fluid compartment 131 provided with through holes 132 for producing a coarse bubbling of air or another suitable gas at the exterior side of membrane 12. The through holes 132 are advantageously provided through the front exterior layer 111 and/or the back exterior layer 112 with the fluid compartment 131 being advantageously arranged between the exterior layers 111 and 112. The through holes 132 are advantageously not covered by the membrane layer 12 and they directly access the exterior side of membrane 12. Fluid compartment 131 is advantageously arranged at a bottom edge 115 of the interior space 110. By way of example, fluid compartment 131 may have a longitudinal axis parallel to the bottom edge 115 of the interior space and/or parallel to any one of the exterior layers 111 and 112. Fluid compartment 131 is advantageously vertically aligned with the interior space 110. A supply duct 133 may feed the air or another suitable gas to fluid compartment 131 from a supply port 103.

The outlet and inlet ports 101 and 102, and the supply port 103 are advantageously arranged at a top edge 116 of the housing 11/interior space 110. In such case, supply duct 133 may extend along one or both opposite side edges 117 and 118 of the interior space and be separated from it through a nonporous wall 119.

The supply port 103 may be connected, in operation, to an air or gas supply system 61 of a bioreactor 60 as shown in FIG. 5, which may or may not recirculate the air or gas within the bioreactor vessel 62 in which a plurality of membrane assemblies 10 or 30 are mounted. It will be convenient to note that the membrane assemblies 10, 30 may be arranged in the bioreactor 60 in any suitable orientation which may deviate from vertical placement. The gas supply system is in fluid communication with holes 132 which provide for gas bubbling of the recirculated gas within vessel 62. Baffles 621 may be arranged within vessel 62 to separate channels 622 of upwards flow of gas bubbles 600 and feed 620 from channels 623 of downwards flow of the feed 620, also referred to as downcomers.

The combined provision of an internal recirculation system and an external (re)circulation system to a membrane assembly allows for simultaneously refreshing liquid at both sides of the semi-permeable membrane 12, which greatly improves diffusion through the membrane and allows better control of and more uniform operation of such membrane assemblies. This is e.g. true for the diffusion of compounds from the exterior side of the membrane to the interior space of the assembly and is advantageously also true for any diffusion of products from the interior space of the assembly to the exterior side, where the products can be collected according to possibly known techniques. Furthermore, an independent control of operational conditions for the exterior side (feed component) and the interior side (encapsulated biomass) becomes possible.

One further advantage of having the duct system 13, in particular the aeration holes 132, integrated into the housing 11 of the membrane assembly, is that a more uniform refreshment of the liquid substrate or feed over the exterior of each membrane 12 can be obtained. This is particularly useful for bioreactors comprising large stacks of membrane assemblies and allowing to provide uniform operation for all assemblies in the stack.

Yet another advantage is that the duct system 13 can be cost effectively integrated in the membrane assemblies described herein, allowing for reducing the overall complexity and footprint of bioreactors.

After manufacturing a membrane assembly, the assembly can be filled with biomass including microorganisms, and/or enzymes, and mounted in a bioreactor. The bioreactor is supplied with a liquid, such as a feed for the biomass encapsulated in the interior space of the assembly. The membrane assemblies are at least partially immersed in the liquid. Nutrients and other useful compounds may then penetrate from the liquid through the membrane into the interior space of the membrane assembly, where they are used or converted by the microorganisms and/or enzymes to produce a desirable product. The diffusion of any of these compounds through the membrane—either from the exterior to the interior space, or from the interior space to the exterior, or both—is typically concentration gradient dependent. Greater concentration gradients lead to higher flux of the compounds through the membrane. The recirculation of the biomass within the interior space and of the liquid at the exterior of the membrane according to aspects presented herein advantageously allows for maintaining higher concentration gradients and therefore higher flux. In such applications, the membrane 12 can be considered as a contactor.

The membrane 12 is advantageously attached to the front layer 111 at a multitude of points distributed across the membrane area portion. The front layer 111 acts as a membrane support in such case. One possibility to obtain attachment is to apply a membrane forming solution on the layer 111 and coagulating or curing the solution according to known techniques.

The membranes as referred to in the present description can be obtained by subjecting a polymer solution to a phase separation process. Phase separation, which is also referred to as phase inversion, is a well-known process wherein demixing between the polymer and the solvent is induced. As a result of demixing, the polymer precipitates, thereby forming a membrane lattice with a desired structure (pore size, pore structure, etc.). Further process steps can be carried out in order to remove the solvent completely (e.g., washing) and to obtain a final pore structure (e.g., removing pore formers). Demixing can be induced based on several techniques. One possibility is thermally induced phase separation (TIPS), wherein demixing is induced by a temperature change at the interface of the polymer solution. Another possibility is to induce a chemical reaction in the polymer solution, causing demixing. This is referred to as reaction induced phase separation (RIPS). However, in the vast majority of cases, demixing is induced by phase diffusion. The polymer solution is contacted with another phase, being a liquid (liquid induced phase separation or LIPS), or a gas (vapour, referred to as vapour induced phase separation or VIPS), which is a non-solvent of the polymer but which is miscible with the solvent of the polymer solution. The liquid or vapour will diffuse through the polymer solution and cause a local change in the polymer solution composition, inducing demixing. As a result, the polymer precipitates from the solution. LIPS is also referred to as immersion precipitation. It will be convenient to note that any phase separation process can be applied to prepare the membranes as described herein.

The membrane comprises or consists of an advantageously thermoplastic polymer compound, which will be referred to hereinafter as the first polymer compound. The first polymer compound is the principal, characteristic or primary polymeric compound used for preparing the membrane forming solution, e.g. the polymer compound present in largest amount in the membrane forming solution. The first polymer compound can be polysulfone (PSU), polyethersulfone (PESU), a grafted variant of them, or a copolymer of either one of the polymers. The first polymer compound can be polyvinylidene fluoride (PVDF), polyvinylidene chloride (PVDC), a grafted variant of them, or a copolymer of either one of the polymers. The first polymer compound can be polyvinyl chloride (PVC), chlorinated polyvinyl chloride (CPVC), a grafted variant of them, or a copolymer of either one of the polymers. The first polymer compound can be a polymer of the polyaryletherketone (PAEK) family, such as polyether ether ketone (PEEK), a grafted variant of any of these polymers, such as sulfonated polyether ether ketone (PEEK-WC), or a copolymer of any one of these polymers. The first polymer compound can be polychlorotrifluoroethene (PCTFE), polyether imide (PEI), polyimide (PI), polyamide imide (PAI), polyacrylonitrile (PAN), polyurethane (PUR), in particular a thermoplastic polyurethane, a grafted variant of any of these polymers, or a copolymer of any one of these polymers. The first polymer compound can be polyphenylene sulphide (PPS), cellulose acetate (CA), cellulose triacetate (CTA), a grafted variant of any of these polymers, or a copolymer of any of these polymers. The copolymers as indicated above can be suitable copolymers of the indicated polymer with any one of polyvinyl chloride, polymethyl methacrylate (PMMA), polycarbonate (PC), cyanoacrylate, cellulose triacetate, polyphenylene sulphide, polystyrene (PS), polyvinyl alcohol (PVA), polyvinyl acetate (PVAc), and polyamides such as polycaprolactam (nylon 6) and nylon-6,6. The first polymer compound can be a suitable blend of two or more of the above listed polymers.

The amount of first polymer compound in the (dry) (final) membrane can be at least 5% by weight, up to at least 50% by weight. The first polymer compound can be an organic binder forming a matrix or lattice of the membrane, in which a possibly hydrophilic filler material is optionally dispersed. The filler material may be organic and is advantageously one or a combination of: hydroxypropylcellulose (HPC), carboxymethylcellulose (CMC), polyvinyl pyrrolidone (PVP), cross-linked polyvinyl pyrrolidone (PVPP), polyvinyl alcohol, polyvinyl acetate, polyethylene oxide (PEO), polyethylene glycol (PEG), and glycerol. Such filler materials can be provided as pore formers and can be removed in a post treatment step, such as by washing in a bleach solution (e.g. for PVP). Other filler materials, which remain in the final membrane layer can be an amine, such as but not limited to one or a combination of: monoethanolamine (MEA), diethanolamine (DEA), polyethylenimine (PEI), aminopropyltrimethoxysilane and polyethylenimine-trimethoxysilane.

The filler material can be an amide or amine containing polymer, such as but not limited to one or a combination of: polyamide (PA), polyurethane (PUR), polyvinylamine (PVAm) and melamine. The filler material may be inorganic, such as one or a combination of $TiO_2$, $HfO_2$, $Al_2O_3$, $ZrO_2$, $Zr_3(PO_4)_4$, $Y_2O_3$, $SiO_2$, carbon, possibly on Pt, Ru or Rh support, $BaSO_4$, $BaTiO_3$, perovskite oxide powder materials, zeolites, metal-organic frameworks (MOF) and silicon carbides. Functionalized variants of the filler materials (such as aminated, sulfonated, acrylated) can be used. Combinations of the above organic and inorganic materials can be used as well as filler material.

The dimensions of the through-holes 113 are not particularly limited and suitable dimensions depend on the application. The through-holes advantageously have a size smaller than or equal to 5 mm, advantageously smaller than or equal to 2 mm, advantageously smaller than or equal to 1.5 mm, advantageously smaller than or equal to 1.2 mm, advantageously smaller than or equal to 1.0 mm. When the holes are too large, smooth coating may be problematic. The through-holes can have a size of at least 5 µm, advantageously at least 10 µm, advantageously at least 25 µm, advantageously at least 50 µm, advantageously at least 100 µm.

The through-holes can be such that the membrane area portion of the layer 111 advantageously exhibits an open area (porosity due to the through-holes) of at least 2%, advantageously at least 5%, advantageously at least 10%, advantageously at least 15%, advantageously at least 20%, advantageously at least 25%, advantageously at least 30%, advantageously at least 35%. The open area is advantageously at most 85%, advantageously at most 70%, advantageously at most 60%, advantageously at most 55%, advantageously at most 50%. The open area refers to the area of the through-holes per unit total area of the layer (including the through-holes), expressed in percentage values. In defining the total area of the layer, any edge region which is not porous, is disregarded. The open area should advantageously be not too low to provide for sufficient flux capability through the layer on the one hand, but neither too high in order not to compromise the stiffness of the housing on the other. It will be convenient to note that the complement of the open area (i.e. 100%—open area) refers to the interfacial surface between membrane and its support, which is the area that is available for bonding the membrane layer to the sheet. Hence also in this regard, the open area should not be too high.

There is no restriction on the cross-sectional shape of the through-holes 113, i.e. they may be circular, square, polygonal, star-shaped or slit-shaped holes, or holes of any other suitable shape.

Referring again to FIG. 4, the semi-permeable membrane 12 can be directly cast from a membrane forming solution on the layer 111. The membrane forming solution may penetrate the through-holes 113 to form plugs 55 at the interior side of layer 111 creating mechanical anchoring points as described in WO 2013/113928 8 Aug. 2013. In addition, or alternatively, the membrane 12 can bond to the exterior surface of layer 111 by molecular entanglement. Such kind of bond, also referred to as solvent bonding and further described in WO 2015/140355 24 Sep. 2015, can be obtained by direct application of a membrane forming solution on layer 111 made of a thermoplastic polymer, where the solvent of the solution is able to soften or at least partially dissolve the polymer of layer 111, enabling molecules of the membrane polymer in solution and molecules of the polymer of layer 111 to interact at the interface. Molecular entanglement is made permanent by precipitation of the polymer from the solution as described above. It will be convenient to note that any other suitable bonding technique, such as ultrasonic welding, can alternatively be used for attaching the semipermeable membrane layer to the support.

Figure 6:
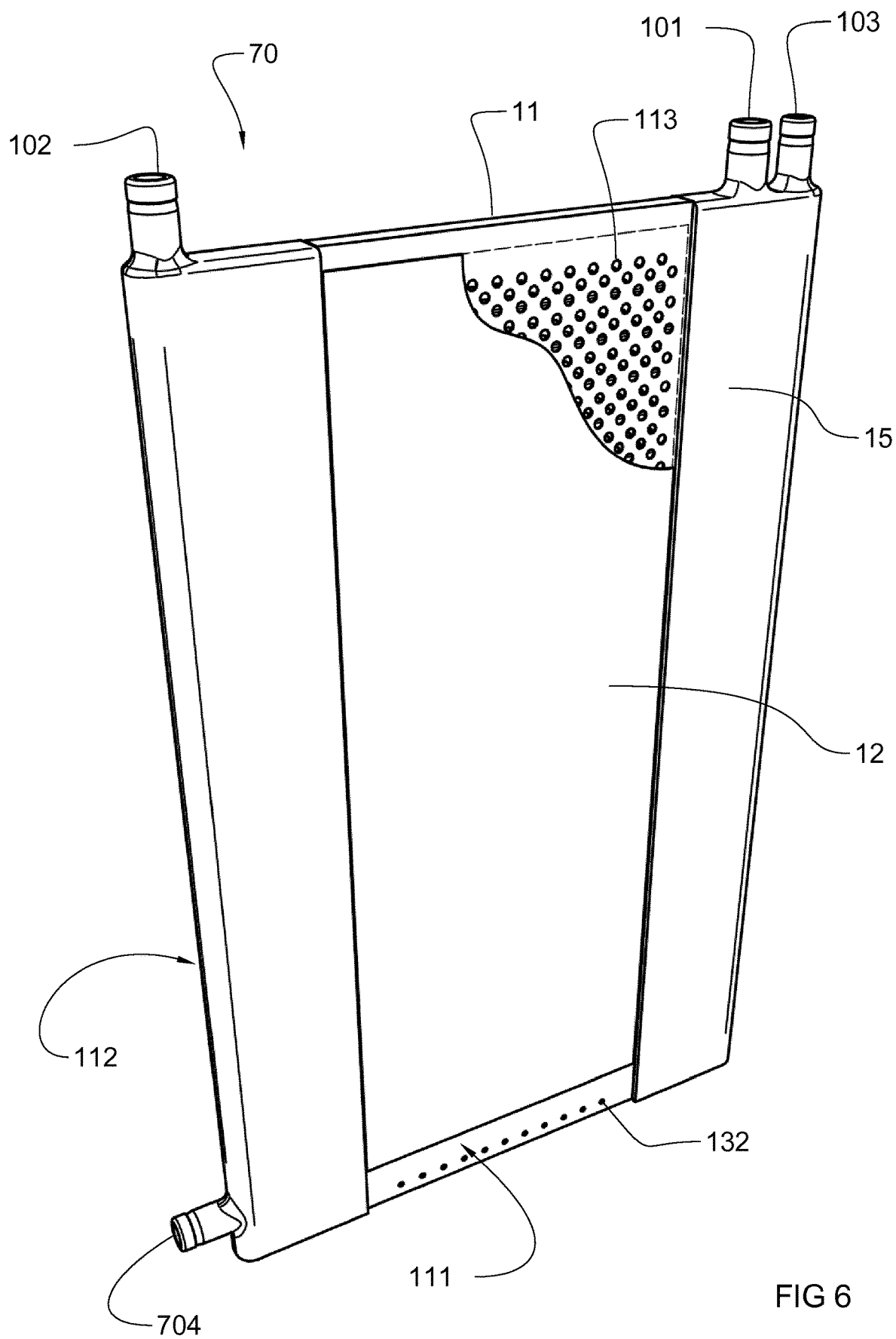
FIG. 6 represents a perspective view of another housing and attached membrane of assemblies according to aspects disclosed herein.
Figure 7:
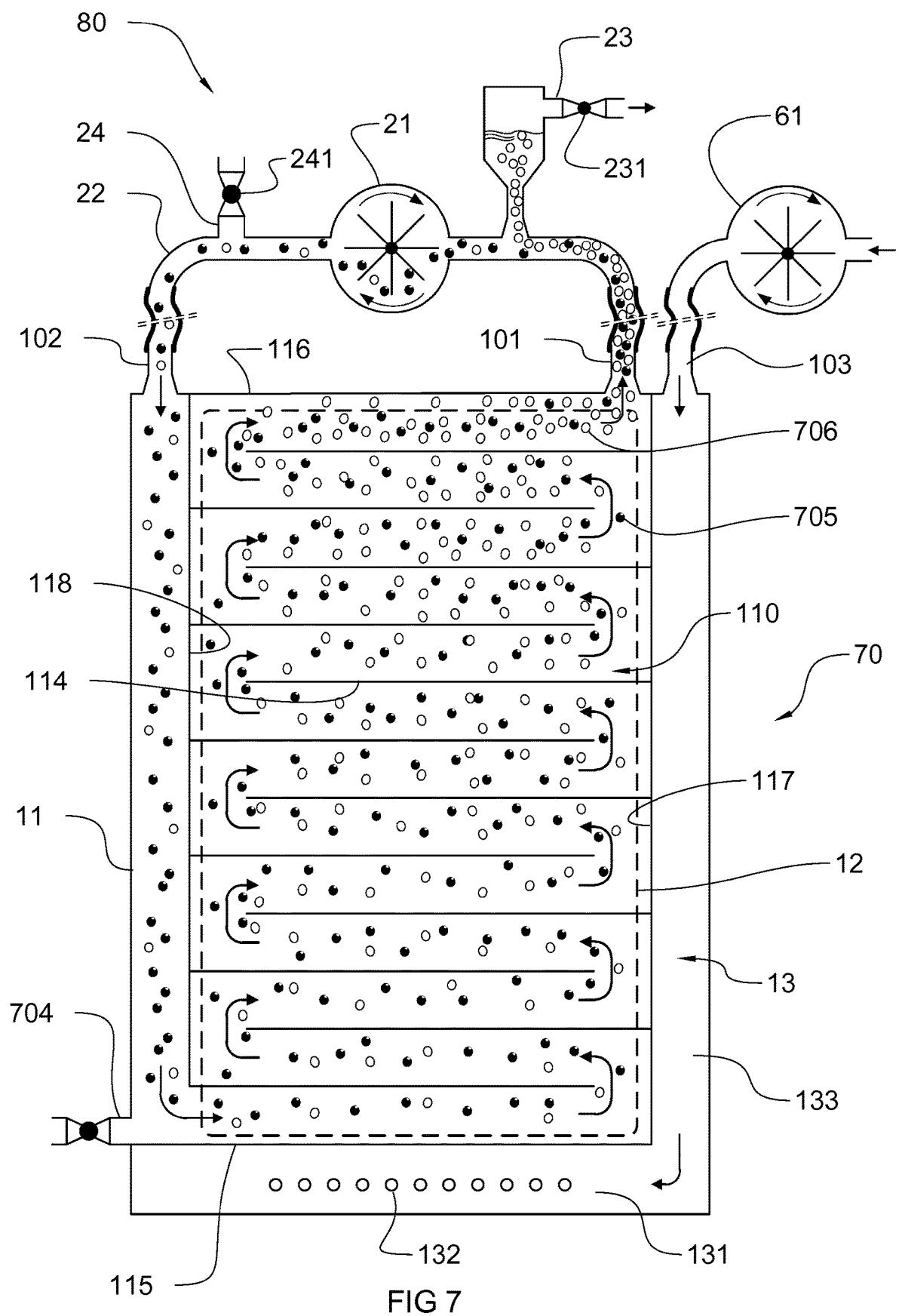
FIG. 7 represents a vertical cross-sectional view of an assembly comprising the housing and membrane of FIG. 6.

Referring to FIG. 6, an alternative example of a membrane assembly 70 is shown, which differs from assembly 10 only in that it further comprises a drain port 704. As shown in FIG. 7, drain port 704 is in fluid communication with the interior space 110 and may serve to drain the content of the interior space 110 in case of maintenance operations and/or to remove excess biomass from the interior space. Still referring to FIG. 7, membrane assembly 70 may be coupled to recirculation system 80 for recirculating the fluid inside interior space 110. Recirculation system 80 differs from recirculation system 20 only in that it comprises an outlet port 24 in fluid communication with duct system 22. A valve 241, e.g. a relief valve, or any other suitable valve system (e.g. a powered valve) is advantageously arranged at outlet port 24 from which a product, which may be liquid, can be harvested (or evacuated). In addition, or alternatively, an outlet port 23 may be provided in fluid communication with duct system 22 and coupled to a valve 231 for harvesting (or evacuating) gaseous products from the interior space. Such gaseous products, which are represented by blank dots 706 in FIG. 7 may be produced by the biomass within interior space 110. These gas bubbles may provide additional cleaning at the internal side of membrane 12, in addition to the cleaning provided by a cross-flow shear of the liquid particles recirculated through interior space 110 by system 80.

It will be convenient to note that not all gas bubbles 706 may be evacuated through port 23 and some bubbles 706 may be entrained through the liquid pump 21 together with e.g. (liquid) inoculum particles, represented by the black dots 705.

As further represented in FIG. 7, recirculation system 80 may be arranged remotely from the membrane assembly 70. Gas supply system 61 is advantageously connected to supply port 103 for supplying gas to supply duct 133.

Figure 8:
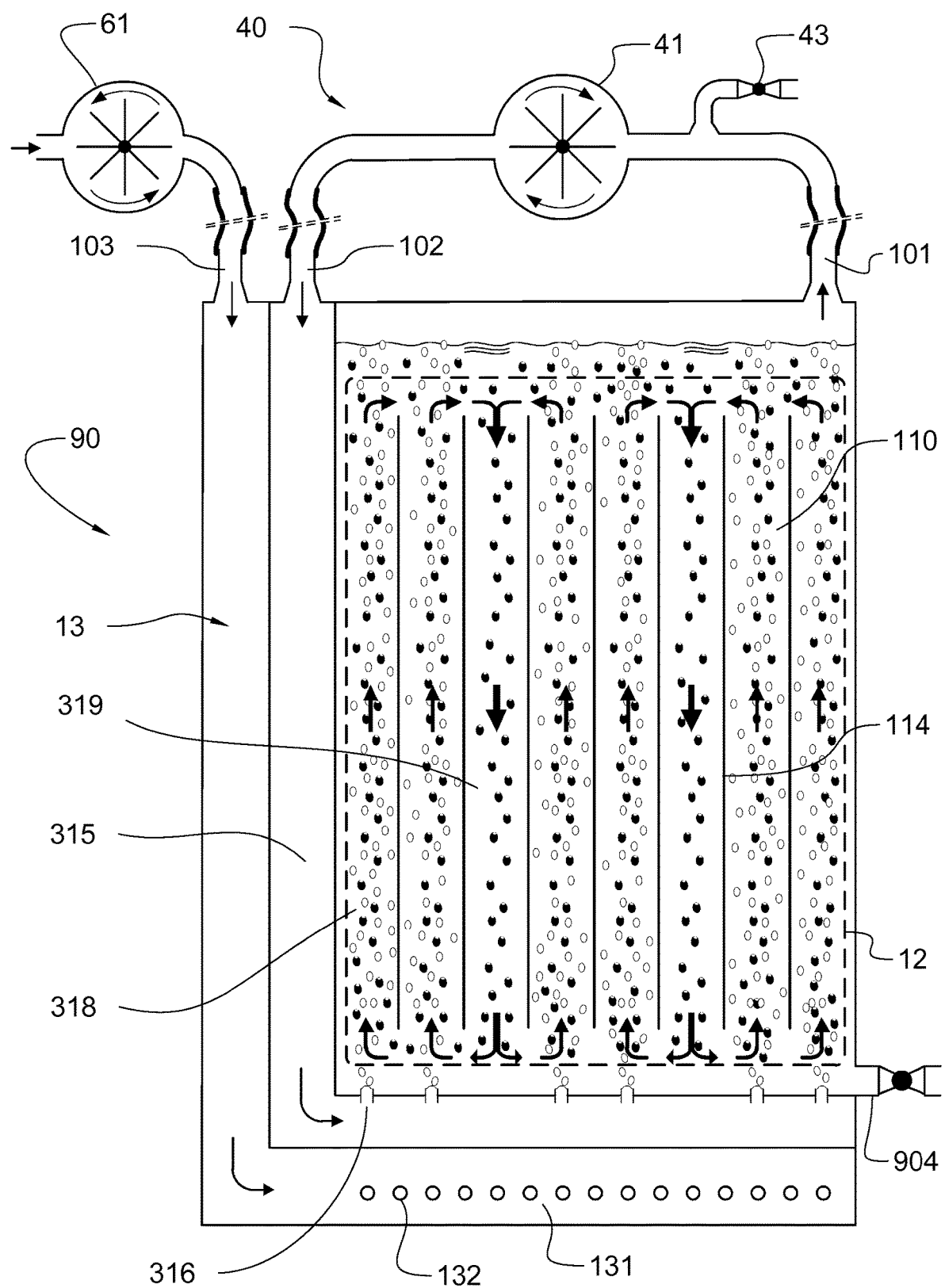
FIG. 8 represents a vertical cross-sectional view of another assembly according to aspects disclosed herein.

Referring now to FIG. 8, an alternative example of an assembly 90 is shown, which differs from assembly 30 in that it further comprises a drain port 904 in fluid communication with interior space 110. Recirculation system 40 is connected to the inlet and outlet ports 102 and 103 of assembly 90 and communicates with the interior space 110. Vent 43 may be used for harvesting or evacuating gas products, while drain port 904 may be used for harvesting or evacuating liquid products. Alternatively, an additional port (not shown) may be provided for harvesting such products. Gas supply system 61 is advantageously connected to supply port 103 for supplying gas to duct system 13.

Figure 9:
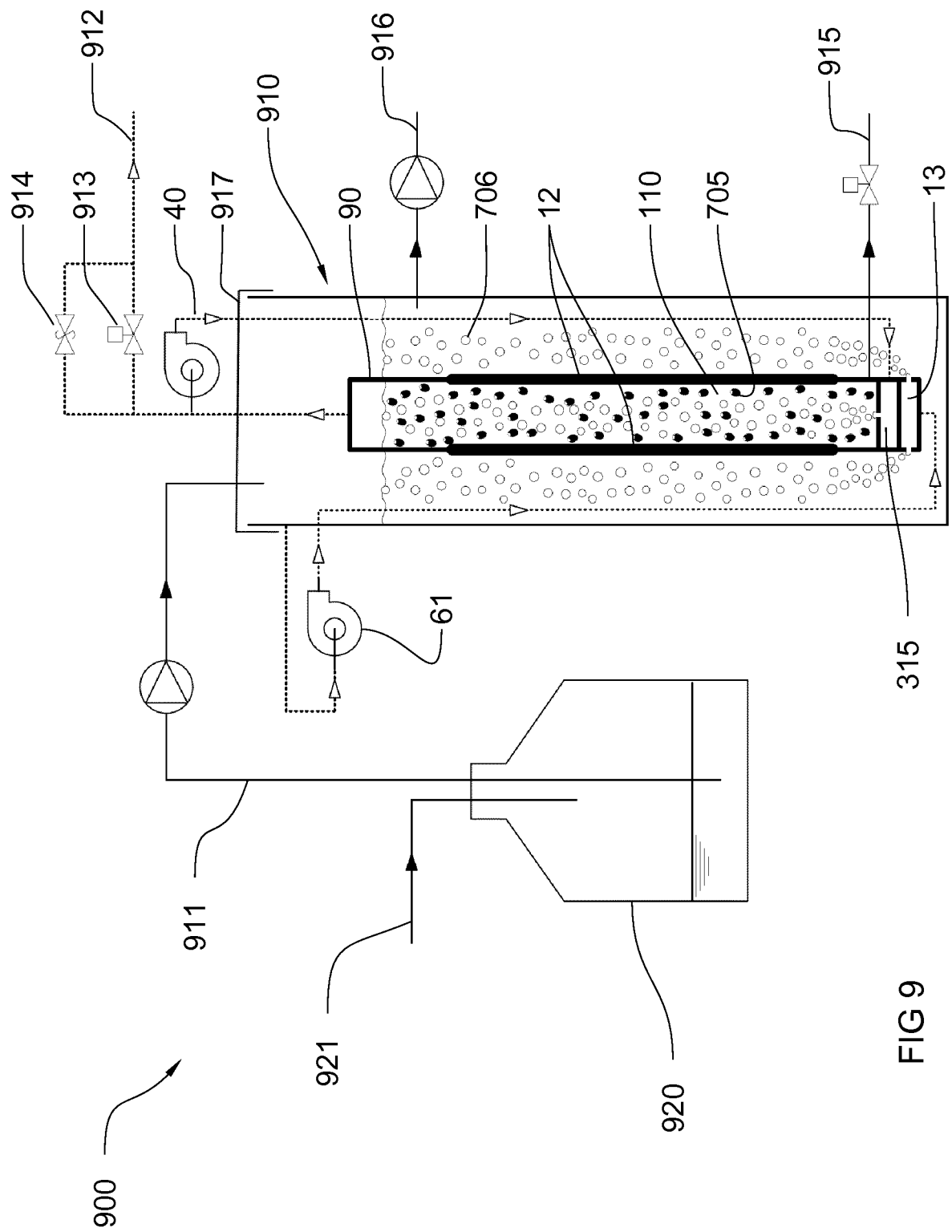
FIG. 9 represents a scheme of a bioreactor plant in which membrane assemblies according to aspects described herein can be used.

Referring to FIG. 9, any of the membrane assemblies described herein 10, 30, 70, 90 can be used in a bioreactor system 900. A plurality of these membrane assemblies are arranged in a bioreactor vessel 910, which may be an open vessel, or closed by cover 917, e.g. in order to ensure operation under sterile conditions. In operation, the interior space of the assembly, e.g. 90, may be filled with a biomass comprising a first inoculum represented by the black dots 705, and which is recirculated through the interior space by recirculation system 40 (or, as the case may be, system 20 described above). An outlet pipe 912 for harvesting gaseous products may fluidly communicate with the interior space 110, e.g. through recirculation system 40. The outlet pipe 912 may comprise either an actuatable (powered) valve 913, or a relief valve 914, or both.

A gas supply system 61 advantageously recirculates gas, represented by the blank dots 706, between the bioreactor vessel 910 and the duct system 13 of assembly 90. This provides cleaning and/or refreshment of the substrate, feed and/or of a second inoculum at an external face of the membranes 12. Liquid products may be harvested either directly from the interior space 110 through outlet port 915, or from the bioreactor vessel 910, at outside of the assembly 90 through outlet port 916, or both through ports 915 and 916. Port 915 may be used as a drain port and/or to remove excess biomass.

Optionally, bioreactor system 900 may comprise a buffer tank 920 in which the substrate or feed may be buffered, and which communicates with bioreactor vessel 910 through a supply pipe 911. Pipe 921 may provide inflow of the substrate or feed to buffer tank 920.

Even though membrane assemblies having a generally rectangular shape have been described above, it will be convenient to note that aspects described herein are not limited to such shapes. By way of example, disc like assemblies can be contemplated as well.

Possible applications for membrane assemblies as described herein are, by way of non-limiting examples:
- fermentation of complex feeds containing high concentrations of inhibitory compounds;
- fermentation of feeds containing a variety of sugar sources (diauxic growth);
- fermentation of feeds with high suspended solid content;
- 2-in-1 fermentations (bioconversions with at least 2 microorganisms in 1 bioreactor) with exchange of metabolites (e.g. production of antibiotics, nutrients, etc. or other products with symbiotic or antagonistic effects);
- controlled co-culture fermentations;
- continuous axenic fermentations without feed sterilization;
- non-sterile mixed culture fermentations.

One possible application is the production of biofuels, such as ethanol, from second generation feedstocks.

The invention claimed is:

1. An assembly, comprising:
a housing comprising a first layer and a second layer opposite the first layer, wherein the first layer and the second layer are spaced apart to define a confined interior space between the first and the second layers,
a semi-permeable membrane attached to the first layer, the semi-permeable membrane covering a porous membrane area portion of the first layer,
an outlet port and an inlet port in fluid communication with the interior space,
first means for circulating a first fluid between the outlet port and the inlet port, and
second means for circulating a second fluid along an exterior surface of the semi-permeable membrane, wherein the second means comprises a fluid duct attached to or integrated within the housing,
baffles arranged in the interior space to produce a serpentine fluid flow path through the interior space,
wherein the semi-permeable membrane forms a barrier allowing for exchange of compounds across the semi-permeable membrane,
wherein the fluid duct is isolated from the interior space and is porous to provide fluid access to an exterior surface of the semi-permeable membrane.

2. The assembly of claim 1, wherein the second means comprise a gas bubbling system configured for supplying gas bubbles along the exterior surface of the semi-permeable membrane thereby entraining a flow of the second fluid along the exterior surface.

3. The assembly of claim 1, wherein the fluid duct is provided with through-holes for producing coarse gas bubbling at the exterior surface.

4. The assembly of claim 1, wherein the fluid duct comprises a porous first portion extending along a bottom edge of the interior space, the first portion being vertically aligned with the interior space.

5. The assembly of claim 4, wherein the interior space is confined between a top edge, a bottom edge and opposite side edges, wherein the fluid duct further comprises a second portion extending along one of the opposite side edges and in fluid communication with the first portion.

6. The assembly of claim 1, wherein the housing further comprises a fluid supply port in fluid communication with the second means.

7. The assembly of claim 1, wherein the first layer and the second layer are planar.

8. The assembly of claim 1, wherein the first layer and the second layer are nonporous thermoplastic polymer sheets, wherein the nonporous thermoplastic polymer sheets comprise through-holes across the membrane area portion.

9. The assembly claim 1, wherein the first means comprise a gas recirculation system.

10. The assembly of claim 9, wherein the first means comprise a gas bubbling system configured for supplying gas bubbles as the first fluid in the interior space.

11. The assembly of claim 1, comprising a second semi-permeable membrane attached to the second layer, the second semi-permeable membrane covering a porous membrane area portion of the second layer.

* * * * *